United States Patent [19]

Kaiser et al.

[11] Patent Number: 4,504,522
[45] Date of Patent: Mar. 12, 1985

[54] METHOD OF MAKING A TITANIUM DIOXIDE OXYGEN SENSOR ELEMENT BY CHEMICAL VAPOR DEPOSITION

[75] Inventors: William J. Kaiser, Farmington Hills; Eleftherios M. Logothetis, Birmingham, both of Mich.

[73] Assignee: Ford Motor Company, Dearborn, Mich.

[21] Appl. No.: 589,790

[22] Filed: Mar. 15, 1984

[51] Int. Cl.³ .............................................. B05D 5/12
[52] U.S. Cl. .................................. 427/103; 427/101; 427/126.3; 427/125; 427/255.3; 338/34; 73/27 R
[58] Field of Search ................... 427/126.3, 126.2, 86, 427/89, 101, 103, 255.3, 123, 125; 338/22 SD, 34; 73/27 R

[56] References Cited

U.S. PATENT DOCUMENTS 3,650,815  3/1972  Ghoshtagore et al. .......... 427/126.3
4,228,128 10/1980  Esper et al. ........................... 428/98
4,234,542 11/1980  Romine ................................. 422/98
4,335,369  6/1982  Taniguchi et al. .................... 338/34

OTHER PUBLICATIONS

Sakurai et al., Rev. Elect. Comm. Lab., 11, 1963, p. 178.

Yokozawa et al., Japan J. of Appl. Phys., 7, 1968, p. 96.

Primary Examiner—Richard Bueker
Attorney, Agent, or Firm—William E. Johnson; Olin B. Johnson

[57] ABSTRACT

A method is disclosed for making a titanium dioxide element which can be used as an oxygen sensing element. The method includes obtaining a substrate for supporting a titanium dioxide film and placing that substrate in a vacuum chamber. A vacuum is drawn on the vacuum chamber and the chamber is heated to a temperature in a range from 400°–700° C. A low pressure carrier gas containing 1–10% by volume of oxygen along with a coating gas formed from an organometallic compound of titanium is flowed over the substrate. The coating gas is one which is heat decomposable into a titanium dioxide coating on the heated substrate. The coating gas and the carrier gas are at a total pressure from 100–200 Pa. The coating gas and carrier gas are flowed over the substrate until a titanium dioxide film of required thickness is built up. After formation of the required thickness of the titanium dioxide film, the substrate is removed from the vacuum chamber and heated to a temperature in a range from 800°–1100° C. for a period of 1–10 hours to transform the film on the substrate to a rutile phase titanium dioxide.

8 Claims, 5 Drawing Figures

TYPICAL RESULTS ON THE DEPENDENCE OF THE RESISTANCE OF $TiO_2$ FILMS ON OXYGEN PARTIAL PRESSURE, $P_{O_2}$, IN THE RANGE 350-850 °C.

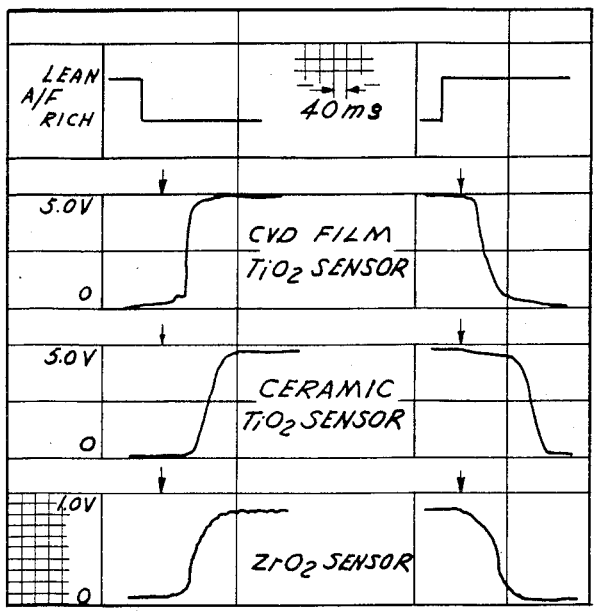

FIG.4

TRANSIENT RESPONSE OF $TiO_2$ AND $ZrO_2$ SENSORS TO LEAN-TO-RICH AND RICH TO LEAN A/F CHANGES DURING A 1.0 Hz SQUARE WAVE MODULATION AROUND STOICHIOMETRY OF THE A/F OF A 2.3 L ENGINE OPERATED AT 2000 R.P.M./60 FT. LB. THE AMPLITUDE OF THE MODULATION WAS 0.5 A/F UNITS. THE ARROWS INDICATE THE APPROXIMATE TIME OF ARRIVAL OF THE LEAN/RICH AND RICH/LEAN GAS FRONTS AT THE LOCATION OF THE SENSORS.

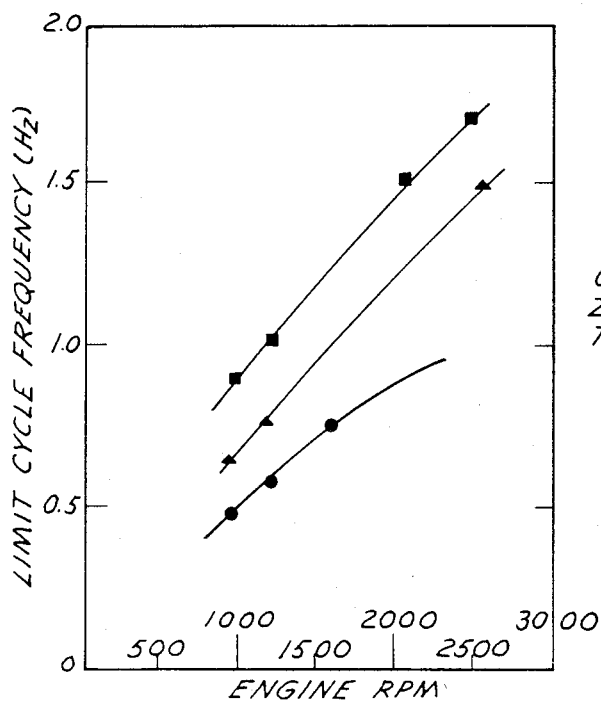

FIG.5

COMPARISON OF $f_{LC}$ OF $ZrO_2$, $TiO_2$ AND CVD FILM $TiO_2$ SENSORS.

METHOD OF MAKING A TITANIUM DIOXIDE OXYGEN SENSOR ELEMENT BY CHEMICAL VAPOR DEPOSITION

TECHNICAL FIELD

This specification is directed to a method of making a titanium dioxide oxygen sensor element. In general, the element so made is characterized as being a "thick film" titanium dioxide sensor element made by chemical vapor deposition.

BACKGROUND AND PRIOR ART STATEMENT

For a number of years, oxygen sensors have been employed in motor vehicles in conjunction with the utilization of three-way catalyst systems for the treatment of exhaust gases from internal combustion engines. Generally, the oxygen sensor and three-way catalyst are coupled with a feedback control system of an air/fuel ratio metering device to control the stoichiometric air/fuel ratio being fed to the internal combustion engine at any particular time. If the oxygen sensor detects too much oxygen in the exhaust gases after passage of those gases through the three-way catalyst, more fuel is supplied to the engine. On the other hand, if the oxygen sensor detects an insufficient amount of oxygen in the exhaust gases, then the feedback control system decreases the amount of fuel being fed to the internal combustion engine.

One type of oxygen sensor which has been developed for such an application uses zirconium oxide, zirconia, as the sensing element. This material has been used in oxygen sensors for millions of automobiles now on the road in the United States.

As an alternate to the zirconium oxide sensor, a titanium dioxide, titania, type of oxygen sensor has been developed by Ford Motor Company. The particular titanium dioxide sensor developed by Ford Motor Company is covered by a number of U.S. patents, see, for example, U.S. Pat. Nos. 3,893,230; 3,911,386; 3,932,246; 3,933,028; 3,959,765; 4,001,758; and 4,151,503.

These patents are representative of the patents Ford Motor Company has obtained in the field of titanium dioxide oxygen sensors. However, these titanium dioxide sensors have a slower response time than the zirconia sensor developed by others. By slower response time we mean that it takes a longer period of time for the titanium dioxide oxygen sensor to detect a switch from oxygen-rich to oxygen-lean conditions, or vice-versa, than does the zirconia sensor.

This slower response of the titania sensor does not have any effect on the feedback control system and, thus engine operation, as long as the response of the feedback control system is limited by a slow fuel metering device such as a feedback carburetor. The inherent mechanical limitations of the carburetor make this device much slower responding than the titania sensor so that the system itself does not in any manner note the slower response time of the titania sensor when this sensor replaces a zirconia type sensor. However, when the feedback control system uses a fast reponse fuel metering device, such as an electronic fuel injection system, then the feedback system could be hampered by the slower response time of a titania oxygen sensor.

The present development was brought about in order to obtain a titania sensor with a faster response time than the previously known titania sensors. It is a principal purpose of our invention to teach titanium dioxide sensors which have response times sufficiently fast that the fuel injected type of feedback system would not notice a delay in receiving a control signal because of a delay in the oxygen sensor's ability to detect changes from oxygen-rich to oxygen-lean conditions and vice-versa. We accomplished this purpose by developing titanium dioxide sensors of the so-called thick film variety which will hereafter be described in greater detail.

The ceramic titanium dioxide ($TiO_2$) materials developed by Ford for oxygen sensing applications, as set forth in the previously cited Ford-assigned patents, have a density in the range from 65–80% of the theoretical value. The microstructure of this type of material consists of interconnected $TiO_2$ particles with a size of a few micrometers and separated by interconnected pores with a similar size. The addition of catalytic metals into the porous $TiO_2$ ceramic accelerates the oxygen transfer process between the solid and the ambient gas and leads to a substantial improvement in the sensor response time in detecting changes in the oxygen content of exhaust gases.

Our studies have indicated that the response time of noble metal impregnated ceramic $TiO_2$ sensors is limited to a large degree by the gas transport process through the pores of the ceramic sensor material. One approach for decreasing the effect of this gas transport process is to decrease the thickness of the $TiO_2$ material; for example, by replacing the ceramic material with a film. If the film is made dense, its thickness must be kept small, less than 10 um (um means micrometers), otherwise oxygen diffusion in the bulk of the solid would result in unacceptably long response times. On the other hand, films with a small thickness, less than 10 um, may not have the required durability since, for example, some erosion of the film would be caused by the constant movement of exhaust gases of an engine thereover. It is thus desirable to prepare films thicker than 10 um, preferably thicker than 20–30 um. However, the response time of sensors using such thick films would be unacceptably long (due to bulk diffusion of oxygen) unless the film has an optimized porosity and microstructure that minimizes the contribution of bulk diffusion and gas transport through the pores to the sensor response delay.

The preparation of films of metal oxides, and $TiO_2$ in particular, has been discussed extensively in the literature. Reported preparation methods include thick film techniques using appropriate printable inks, sputtering, thermal evaporation, and chemical vapor deposition. However, most of the prior art $TiO_2$ film preparation methods are not suitable for oxygen sensor applications because they do not provide the film composition, microstructure, and electrical and mechanical properties required for fast responding oxygen sensors. For example, sputtering deposition tends to give dense films which, as discussed above, would not provide fast oxygen sensors unless their thickness is kept undesirably small. Amorphous films with densities much smaller than theoretical (in the range of 50–80%) have been prepared by various techniques; however, these films are unstable at the high temperatures of the automotive exhaust and do not generally have the required electrical properties. High temperature annealing to convert them to the stable rutile structure has the tendency to change them to dense materials.

A common and commercially used technique for thick film preparation is screen printing from inks. U.S.

Pat. No. 4,335,369 to Taniguchi et al describes a method of preparing thick $TiO_2$ films by screen printing from $TiO_2$ pastes for oxygen sensing applications. Sensors using these films were found to be faster than those employing ceramic $TiO_2$ materials. The method described in the above patent, however, is tedious and time consuming because it was found that the optimum film thickness of 50–100 um with the required microstructure could not be obtained unless the $TiO_2$ paste was deposited in approximately 15 um steps, each step followed by a long drying period (more than one hour).

Another commercially important film preparation technique is the chemical vapor deposition (CVD). Metal oxides including $TiO_2$ have been prepared by CVD from several inorganic and organic compounds. Of the organic compounds, tetraisopropyl titarate $Ti(C_3H_7O)_4$ has been used for the preparation of dense, hard and abrasion-resistant titanium oxide (with unspecified Ti/O ratio) protective coatings of glassware. These materials, however, are amorphous, unstable at elevated temperatures, and do not have the electrical properties required for oxygen sensor applications.

S. Sakurai and M. Watenabe (Rev. Elect. Comm. Lab. 11, 178, 1963) decomposed $Ti(C_3H_7O)_4$ [and $Ti(C_2H_5O)_4$] in vacuum above 900° C. to obtain $TiO_2$ films with the rutile structure. These films, however, were found to be very dense (99% of the theoretical density); this method of $TiO_2$ film preparation is not therefore suitable for obtaining fast $TiO_2$ oxygen sensors.

More recently, Yokozawa et al (Japan J. Appl. Phys. 7, 96, 1968) investigated the preparation of thin titanium oxide films on silicon wafers from $Ti(C_3H_7O)_4$ for possible use in photo-etching technology. They found that thermal decomposition of $Ti(C_3H_7O)_4$ in an atmosphere of nitrogen and oxygen in the range of 320°–540° C. gave films consisting of very fine crystallites of anatase phase. These films are apparently unstable since the anatase phase films were found to possess the remarkable property of being easily etched (4–60 A°/sec.) by a diluted HF solution; in constrast, normal $TiO_2$ cannot be etched with any known etching agent (except KOH above 150° C.).

It is thus desirable to develop $TiO_2$ thick film preparation techniques that provide the microstructure and electrical properties required for fast responding oxygen sensors. The technique developed should be simple and not time consuming so as to be acceptable for high volume production of oxygen sensors. These are some of the objectives that this invention attempts to fulfill.

SUMMARY OF THE INVENTION

This invention relates to a method of making a titanium dioxide element and, more particularly, to a method of making a titanium dioxide element which can be used as an oxygen sensing element.

In accordance with the general teachings of the method of this invention, a titanium dioxide element which can be used as an oxygen sensing element is made in the following manner. A substrate for supporting a titanium dioxide film is obtained. The substrate is placed in a vacuum chamber and a vacuum is drawn on the vacuum chamber so that the substrate is in a vacuum free of water vapor. The substrate is heated in the vacuum chamber to a temperature in a range of 400°–700° C. A low pressure carrier gas is flowed over the heated substrate, the carrier gas containing 1–10% by volume of oxygen. A coating gas is added to the carrier gas for flowing over the substrate. The coating gas is an organometallic compound of titanium which is heat decomposable into a titanium dioxide coating phase and a heat volatilized phase so that in such a manner titanium dioxide is coated onto the heated substrate. The coating gas and the carrier gas are at a total pressure in a range of 100–200 Pa. The addition of the coating gas to the carrier gas is continued and the gases are flowed over the substrate until a titanium dioxide film of a required thickness in a range of 10–150 um is deposited at a rate of 0.1–5 um minute. The oxygen contained in the carrier gas is effective to help putting down a titanium dioxide coating which adheres to the substrate, has the required porosity, and can be heat treated to develop the required oxygen sensing characteristics for the material. The heating of the substrate and the flowing of the gases thereover are terminated when the titanium dioxide film of required thickness is coated on the substrate. Thereafter, the coated substrate is heated to a temperature in a range of 800°–1100° C. for a period of 1–10 hours to transform the titanium dioxide film formed on the substrate to the rutile phase.

A further portion of the specification will teach the particular details of a preferred embodiment of the method of our invention along with variations thereof.

BRIEF DESCRIPTION OF THE DRAWINGS

The novel features that are considered characteristic of the invention are set forth with particularity in the appended claims. The invention itself, however, both as to its organization and its method of operation, together with objects and advantages thereof, will best be understood from the following description of specific embodiments when read in connection with the accompanying drawings, in which:

FIG. 4 is a comparison of the transient response of typical CVD-grown $TiO_2$ film sensor, a ceramic $TiO_2$ sensor, and a $ZrO_2$ sensor; and FIG. 5 is a graphical presentation of the dependence of the frequency of the feedback control of the air to fuel ratio of an internal combustion engine on engine rpm for a CVD $TiO_2$ film, a ceramic $TiO_2$, and a $ZrO_2$ sensor.

BEST MODE AND INDUSTRIAL APPLICABILITY

Figure 1:
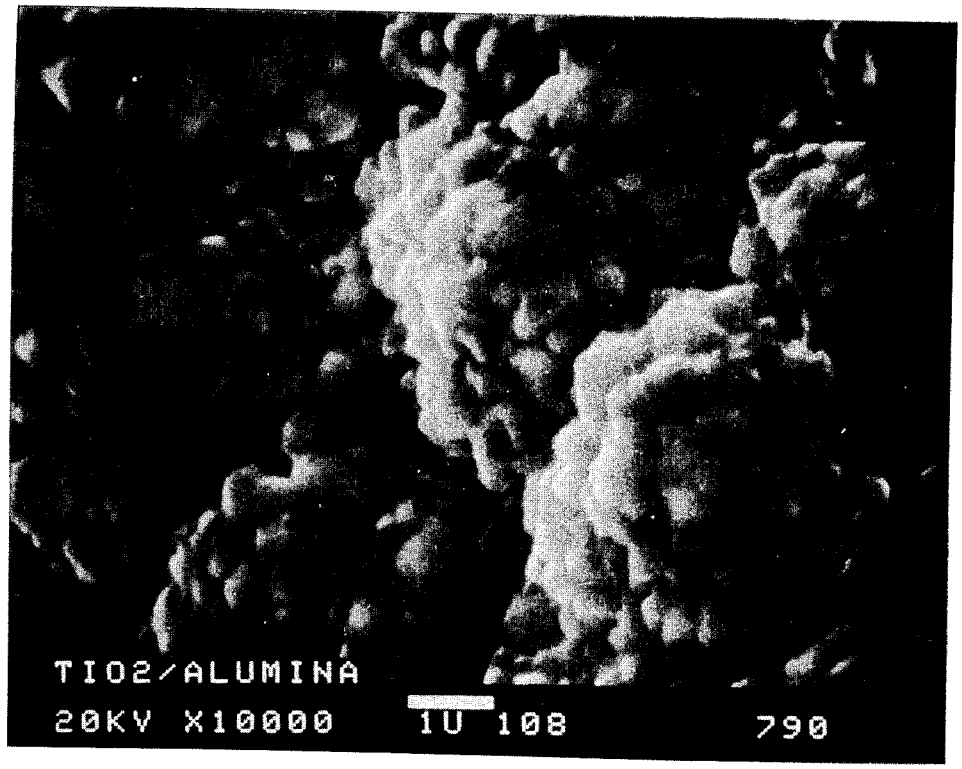
FIG. 1 is a scanning electron microphotograph of a $TiO_2$ film on an alumina substrate after annealing thereof as prepared according to a preferred embodiment of the present invention.

The following description is what we consider to be a preferred embodiment to the method of our invention of making a titanium dioxide element which can be used as an oxygen sensing element. The following description also sets forth what we now contemplate to be the best mode of carrying out the method of our invention. The description is not intended to be a limitation upon the broader principles of the method and while preferred materials are used to illustrate the preferred embodiment it does not mean that other materials cannot be used in the method of this invention.

Chemical vapor deposition (CVD) is a deposition process in which the material deposited on a substrate is the product of chemical reactions. The heart of a CVD apparatus is a reactor in which the chemical reactions occur in order to deposit one of the reaction products. An appropriate substrate is placed in the reactor and generally heated to a desired temperature by some type of heating arrangement which is well known to the skilled artisan. The reactants are introduced into the reactor in a manner well known in the art using appropriate carrier gases.

In order to make a titanium dioxide film for oxygen sensor applications by chemical vapor deposition, the source material, or coating gas, is preferably an organometallic compound of titanium. The preferred compound is tetraisopropyl titanate, $Ti(C_3H_7O)_4$. This material offers several advantages for CVD deposition as it is sufficiently volatile to exert an appreciable vapor pressure at relatively low temperatures without excessive decomposition. This compound melts at 20° C. and boils at 233° C. at 1 atmosphere pressure and at 58° C. at 1 mm Hg pressure. Also, this compound decomposes easily on heated, solid surfaces to form an oxide film. As an additional matter, this material is relatively safe to handle without corrosion problems. It is soluble in many common organic solvents, but it decomposes in water. DuPont produces this material under the trade name Tyzor-TPT.

In accordance with our preferred embodiment, our preferred organometallic compound is placed in an evaporator and the substrates to be coated are mounted on a resistive heater inside of a reactor in which the CVD operation is to take place. Alternatively, if the skilled artisan desired, the substrates may be heated by RF heating of a conductive susceptor or by infrared illumination of the substrate.

The optimum conditions which we have established for our preferred method of depositing films having the required electrical and structural properties for high performance fast oxygen sensors are shown in Table I.

TABLE I

| Substrate Temperature | 550–650° C. |
| Carrier Gas | 5% $O_2$/Ar (Dry) |
| Pressure at Deposition | 130 Pa |
| Growth Rate | Several u/min. |
| Substrate | Pt, $Al_2O_3$, Quartz |

In a typical run, the substate to be coated is first heated in a vacuum of a vacuum chamber (established, for example, with a mechanical pump) to a temperature between 550°–650° C. The vacuum as drawn is one which eliminates water vapor from the system.

A flow of the carrier gas consisting of a few percent $O_2$ in argon, nitrogen, or some other suitable inert gas composition, preferably argon, is then directed over the substrate where the pressure in the vacuum chamber rises to a value in the range of 10–50 Pa. Oxygen is included in the carrier gas in a range from 1–10% by volume, preferably 3–7% by volume, most preferably 5% by volume. Subsequently, the organometallic compound vapors, which is the coating gas, are introduced into the carrier gas upstream of the substrate to bring the total pressure in the vacuum chamber to a value in the range of 100–200 Pa, preferably 130 Pa. Under these conditions, the deposition rate of the titanium dioxide film on the substrate is at several um/min, for example, in a range of 0.1–5 um/minute. It is noted that such deposition rates are vastly higher than those used in the prior art of Yokozawa et al. The resulting $TiO_2$ film is allowed to build up to a thickness in a range of 10–150 um for oxygen sensor applications.

The presence of oxygen in the carrier gas was found to be necessary by us for the method of our invention for the formation of workable titanium dioxide films. In the absence of oxygen, the films were dark in appearance and conained excess titanium. Subsequent high temperature oxidation of these Ti-rich films in air (or oxygen) did not give films with properties, e.g., electrical, as good as those of the films grown in the presence of a controlled amount of $O_2$.

It is also important to keep the system relatively free of water vapor. Homogeneous reaction/nucleation in the gas phase between water vapor and coating gas can lead to snow-like deposits on the substrate (and on all available surfaces in the vacuum chamber) with poor adhesion and other poor physical properties for the deposited film.

Films grown under the preferred conditions of the method of our invention described above are mainly of the anatase phase of titanium dioxide. This $TiO_2$ phase is not the phase required for sensor applications. However, a subsequent heat treatment after the formation of the anatose phase film at a temperature in the range of 800°–1100° C. for 1–10 hours, preferably 1–3 hours, converts this phase into the rutile phase required for sensor applications.

FIG. 1 of the drawings shows a scanning electron microscope image of a typical $TiO_2$ film on alumina substrate. The films generally show a rather pronounced columnar growth and have porosity. This film microstructure is stable in its annealed form. The microstructure shown in FIG. 1 allows $TiO_2$ films as thick as 100–150 um or more to have excellent transient response characteristics to the partial pressure of oxygen as discussed below.

The film microstructure was found to depend somewhat on the nature of the substrate. In accordance with our preferred teachings, the substrate used is an alumina substrate. Other suitable materials may be used, however, depending upon the exact properties desired. For example, platinum or other high temperature environment resisting substrates may be used if desired.

The final step in the preparation of a preferred $TiO_2$ film oxygen sensor element, according to the present invention, is to heat the CVD film with a water solution of $H_2PtCL_6$ or of a $H_2PtCL_6/RhCL_3$ mixture, dry it in air, and subsequently heat it at a temperature around 900° C. The purpose of this optional but preferred treatment is to add a catalyst to the $TiO_2$ oxygen sensing material. The addition of noble metal catalyst resulting from this treatment contributes to the high performance operation of $TiO_2$ sensors based on these films at high and low exhaust gas temperatures.

It should be appreciated from the discussion above that the preparation of $TiO_2$ films with optimized properties is achieved by the method of this invention in a simple process which can be well controlled in a production environment and can therefore be used efficiently for large scale production of high performance $TiO_2$ oxygen sensors. This method thus overcomes some of the limitations of the methods of the prior art.

Figure 2:
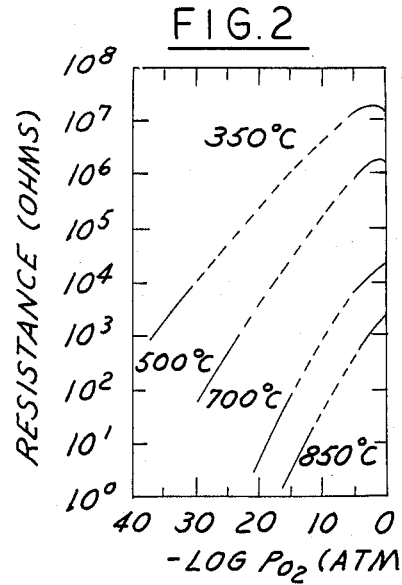
FIG. 2 is a graphical presentation of the dependence of the resistance of a CVD-grown $TiO_2$ film on the ambient oxygen partial pressure at various temperatures from 350° C. to 850° C.

FIG. 2 shows some typical results on the dependence of the electrical resistance of preferred CVD grown $TiO_2$ films impregnated with Pt/Rh catalyst on the oxygen partial pressure in the temperature range of 350°-850° C. At low P$_{O2}$, the films are n-type and the slope of the log R vs. log P$_{O2}$ curve is approximately ¼ for temperatures above about 400° C. At the high P$_{O2}$ range, the resistance tends to saturate with P$_{O2}$ at the higher temperatures and shows a maximum at the lower temperatures. Beyond the maximum, the materials are p-type. This behavior is less pronounced in the CVD films than in the ceramics where a maximum is usually observed even at the higher temperature. The difference appears to be due to the higher purity of the CVD films. This finding is important because it results in a larger change in the CVD TiO$_2$ element resistance when the A/F ratio of an internal combustion engine is changed through stoichiometry because a larger change alleviates the effect of varying temperature and the effect of aging of the sensor element.

Figure 3:
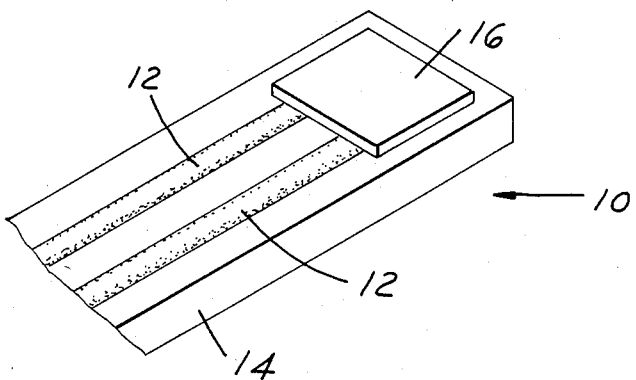
FIG. 3 is a schematic drawing of a CVD-grown $TiO_2$ film sensor according to a preferred embodiment of the present invention.

A sensor element 10 was constructed in accordance with the method of this invention in an embodiment as shown in FIG. 3. Two platinum strips 12—12 were deposited on an insulating alumina substrate 14 to provide electrical contacts. A TiO$_2$ film 16 was subsequently deposited on the substrate by chemical vapor deposition (CVD) as described above. The platinum strips may be deposited after the titanium dioxide film has been deposited, if desired. The TiO$_2$ elements were finally treated with a noble metal catalyst. It is appreciated that sensing element configurations other than that shown in FIG. 3 are possible, the embodiment of FIG. 3 being only one example of the application of the present invention of preparing by chemical vapor deposition TiO$_2$ films with exceptional properties. These TiO$_2$ sensing elements were mounted on 18 mm spark plug structures for internal combustion engine use.

FIG. 4 compares the transient response of a CVD TiO$_2$ film sensor with those of a ceramic TiO$_2$ and ZrO$_2$ sensors. In this test, an internal combustion engine was operated at 2000 rpm and the A/F ratio was changed from lean to rich A/F values and vice-versa. The temperature of the sensors was about 650° C. In the case of the TiO$_2$ sensors, a 5.0 volt power supply voltage was applied across the series combination of the oxygen sensing element and a resistor, and the sensor output voltage was measured across the resistor. As shown in FIG. 4, the TiO$_2$ film sensor is not only substantially faster than the ceramic TiO$_2$ sensor, but also faster than the ZrO$_2$ sensor. The faster transient response of the CVD grown TiO$_2$ film sensor is reflected in its HF feedback control performance.

FIG. 5 compares the frequency of the HF feedback control of the engine when each sensor was used. The CVD TiO$_2$ film sensor gives the highest frequency as expected from the fact that it has the shortest response time. A higher frequency generally results in a smaller amplitude excursion of the A/F ratio around stoichiometry and should lead to an improved system performance.

In summary, this invention describes a simple and inexpensive method, and defines the necessary conditions to obtain on a desired substrate a thick, stable and mechanically strong film of titanium dioxide having not only the necessary electrical properties for oxygen sensing applications, but also an optimized microstructure that provides a fast responding sensor by minimizing the composite effect on the transient sensor response of the various processes defining the equilibration of the material to change in the ambient oxygen atmosphere.

While particular embodiment of the method of our invention have been illustrated and described, it will be obvious to those skilled in the art that various changes and modifications may be made for our method without departing from the invention. It is intended to cover in the appended claims all such modifications and equivalents as fall within the true spirit and scope of this invention.

We claim:

1. A method of making a titanium dioxide element which can be used as an oxygen sensing element, which method comprises the steps of:

obtaining a substrate for supporting a titanium dioxide film;

placing said substrate in a vacuum chamber;

drawing a vacuum on said vacuum chamber;

heating said substrate in said vacuum chamber to a temperature of 400°-700° C.;

flowing a low pressure carrier gas over said heated substrate, said carrier gas containing 1-10% by volume of oxygen;

adding a coating gas to said carrier gas for flowing over said substrate, said coating gas being an organometallic compound of titanium which is heat decomposable into a titanium dioxide coating phase and a heat volatilized phase, whereby titanium dioxide is coated onto said heated substrate, said coating gas and said carrier gas being at a total pressure from 100-200 Pa;

continuing the addition of said coating gas to said carrier gas and flowing of said gases over said substrate until a titanium dioxide film of a required thickness in a range from 10-150 um is built up on said substrate at a rate of 0.1-5 um per minute;

terminating said heating of said substrate and said flowing of said gases over said substrate when said titanium dioxide film of required thickness is coated on said substrate; and heating said coated substrate to a temperature in a range from 800°-1100° C. for period of 1-10 hours to transform said titanium dioxide film formed on said substrate to a rutile phase with a stable, porous microstructure.

2. A method of making a titanium dioxide element as defined in claim 1, wherein: said rutile phase titanium dioxide film is also impregnated with a noble metal catalyst.

3. A method of making a titanium dioxide element as defined in claim 1, wherein: said carrier gas is selected from the group consisting essentially of argon, nitrogen, and mixtures of argon and nitrogen.

4. A method of making a titanium dioxide element which can be used as an oxygen sensing element, which method comprises the steps of:

obtaining a substrate for supporting a titanium dioxide film;

placing said substrate in a vacuum chamber;

drawing a vacuum on said vacuum chamber;

heating said substrate in said vacuum chamber to a temperature of 550°-650° C.;

flowing a low pressure carrier gas over said heated substrate, said carrier gas containing 3-7% by volume of oxygen;

adding a coating gas to said carrier gas for flowing over said substrate, said coating gas being tetraisopropyl titanate which is heat decomposable into a titanium dioxide coating phase and a heat volatilized phase, whereby titanium dioxide is coated onto said heated substrate, said coating gas and said carrier gas being at a total pressure from 100–200 Pa;

continuing the addition of said coating gas to said carrier gas and flowing of said gases over said substrate until a titanium dioxide film of a required thickness in a range from 10–150 um is built up on said substrate at a rate of 0.1–5 um per minute;

terminating said heating of said substrate and said flowing of said gases over said substrate when said titanium dioxide film of required thickness is coated on said substrate; and heating said coated substrate to a temperature in a range from 800°–1100° C. for period of 1–10 hours to transform said titanium dioxide film formed on said substrate to a rutile phase with a stable, porous microstructure.

5. A method of making a titanium dioxide element as defined in claim 4, wherein: said carrier gas contains 5% by volume oxygen.

6. A method of making a titanium dioxide element as defined in claim 4, wherein: said coating gas and said carrier gas are at a total pressure of about 130 Pa.

7. A method of making a titanium dioxide element as defined in claim 4, wherein: said heating of said coated substrate is for a period of 1–3 hours to form said rutile phase.

8. A method of making a titanium dioxide element as defined in claim 4, wherein: said rutile phase titanium dioxide film is also impregnated with a noble metal catalyst.

* * * * *